United States Patent [19]

Gindler

[11] 4,072,627

[45] Feb. 7, 1978

[54] URIC ACID DETERMINATION

[75] Inventor: E. Melvin Gindler, Rockford, Ill.

[73] Assignee: Pierce Chemical Company, Rockford, Ill.

[21] Appl. No.: 710,801

[22] Filed: Aug. 2, 1976

[51] Int. Cl.$^2$ .................. C09K 3/00; G01N 31/06; G01N 31/22; G01N 33/16
[52] U.S. Cl. .................. 252/408; 23/230 B; 195/103.5 R; 356/39; 424/7
[58] Field of Search .................. 252/408; 23/230 B; 195/103.5 R; 356/39; 424/7

[56] References Cited

U.S. PATENT DOCUMENTS

| | | | |
|---|---|---|---|
| 3,282,649 | 11/1966 | Bittner | 252/408 |
| 3,528,777 | 9/1970 | Moran | 23/230 B |
| 3,536,448 | 10/1970 | Patel | 23/230 B |
| 3,649,198 | 3/1972 | Rush | 23/230 B |
| 3,711,252 | 1/1973 | Roy | 252/408 |
| 3,794,467 | 2/1974 | Adams et al. | 23/230 B |
| 3,822,115 | 7/1974 | Morin et al. | 252/408 |
| 3,920,400 | 11/1975 | Schreibe et al. | 23/230 B |
| 3,928,137 | 12/1975 | Monte et al. | 23/230 B |

OTHER PUBLICATIONS

Mopper, K., et al., Anal. Biochem., vol. 56, pp. 440-442 (1973).
Gindler, E. M., Clinical Chemistry, vol. 16, No. 6, p. 519 (1970).

*Primary Examiner*—Benjamin R. Padgett
*Assistant Examiner*—T. S. Gron

[57] ABSTRACT

An aqueous solution useful in connection with a redox type spectrophotometric or colorimetric determination of uric acid in a biologic fluid is disclosed. The solution contains either a multivalent metallic ion reducible to a lower valence state by uric acid, a water soluble chelating compound capable of complexing with a metallic ion after reduction by uric acid to yield, in complexed form, a colored complex, or a combination of said ion and said chelating compound. The solution also contains, as an added constituent, imidazole, an alpha-amino acid, or a combination thereof. This constituent is present in an amount such that, when said solution contains a biologic fluid containing protein and uric acid, a buffer system such that the pH of the solution is 6 to 12, and a multivalent metal ion, the protein in the fluid does not significantly reduce said multivalent ions present in the solution.

10 Claims, No Drawings

URIC ACID DETERMINATION

The present invention relates to the determination of uric acid in biologic fluids, and, more particularly, to avoiding protein interference in such a determination.

In the human body, uric acid is the final product of the metabolism of purines, especially adenine and guanine, which are constituents of all nucleic acids. In most other mammals, uric acid is further broken down by the enzyme uricase to allatonin which is highly soluble. However, man does not possess uricase and, as a result, uric acid is not broken down further in the human body and this can lead to the possibility of elevated serum uric acid concentrations, typically termed hyperuricemia. In turn, hyperuricemia can give rise to the clinical syndrome of gout. Testing for uric acid in human sera is, therefore, a commonly employed clinical diagnostic procedure.

A redox type of spectrophotometric or colorimetric determination for uric acid is a common approach. Uric acid is recognized as being a reductant of multivalent metallic ions and, in the redox approach, this function is utilized. Thus, the serum sample containing the analyte uric acid is added to a reagent solution containing a multivalent metallic ion, the degree of reduction of the metallic ions originally present being indicative of the concentration of analyte uric acid in the serum sample. So that the degree of reduction can be quantitatively ascertained spectrophotometrically or colorimetrically, there is also present in the reagent solution a binding compound which is capable of complexing with the metallic ion, after reduction by uric acid, to yield, in the so complexed form, a colored complex. The color intensity of the complex is correlatable with the degree of metallic ion reduction and, in turn, the concentration of uric acid can be determined from a calibration graph constructed from known uric acid concentrations.

There are three common redox type systems now in use. One is the phosphotungstic method wherein uric acid acts to reduce tungsten (VI) to yield the characteristic tungsten blue color, the measurement of which is accomplished at 640 to 720 nm. The other two methods are similar in that uric acid acts as the reducing agent for reducing divalent copper ($Cu^{++}$) to monovalent copper ($Cu^+$) and in the use of a chelating compound which contains two aromatic rings, each of which has a heterocyclic nitrogen atom which combine in complexing with a monovalent copper ion to develop a characteristic color. There are two of such chelating compounds in common use; one being neocuproine and the other 2,2'-bicinchoninate. These compounds, which have the following structural representations, are commonly utilized in the form of the hydrochloride, trihydrate and disodium salts, respectively.

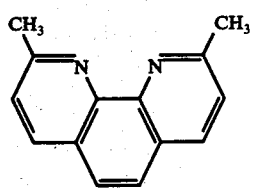

Neocuproine

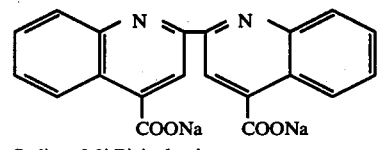

Sodium 2,2'-Bicinchoninate

With neocuproine, a yellow color is developed in the presence of $Cu^+$ which is measured at 455nm. With the bicinchoninate, a lavender color is formed and absorbance measured at 562nm.

A problem which can be encountered with these redox type determinations of uric acid stems from the fact that the reduction reaction involved is not entirely specific for uric acid, there being other constituents in biologic fluids which also tend to reduce the multivalent ions employed. Except for protein, this problem has been largely overcome by using as the blank, against which the reagent solution containing the serum sample is measured, an identical solution except for the addition thereto of uricase. The uricase in the blank specifically destroys the serum uric acid therein, thus the resulting absorbance is singularly attributable to the interfering substances in the sample which have reduced the multivalent ions. In turn, the difference between the reagent solution with no uricase and the blank is representative of the analyte uric acid concentration in the serum.

As to protein, this is a reductant for multivalent ions in alkaline pH. And, since the customary redox methods are accomplished at a pH within the range 6 to 12, protein interference can be a serious problem. Protein is, of course, present in a much larger concentration in serum than is uric acid and, therefore, its reductive effect on the multivalent ion can in essence swamp the effect of uric acid. Accordingly, even utilizing a blank containing uricase, the sensitivity of the resulting measurement is simple inadequate for reliable determinations of uric acid unless the reductive effect of protein is largely eliminated. With respect to the use of the phosphotungstic and bicinchoninate methods, protein removal, such as by dialysis, before determination is ordinarily employed. With neocuproine, there are several test procedures commercially available which apparently do not require protein removal. The manner in which the problem with respect to protein interference is avoided is not now known.

In accordance with the present invention, there is provided an aqueous solution which is useful in connection with a redox type spectrophotometric or colorimetric determination of uric acid in a biologic fluid which does not necessitate the removal of protein prior to determination. An important aspect thereof resides in the discovery that imidazole or a water soluble alpha-amino acid can be used to prevent or diminish protein reduction of a multivalent metal ion while not interfering with the reducing action of uric acid on the ion. Accordingly, by including one of these constituents in the reagent solution or in one of the solutions used in formulating the reagent solution, the determination of uric acid can be accomplished without the necessity for prior protein removal. The invention is considered to be applicable with respect to redox systems as discussed above. Accordingly, any of the solutions illustrated herein can, in keeping with conventional practices, contain preservatives and fillers as well as buffer systems such that the pH of the reagent solution, after addition of the biologic fluid thereto, is within the range 6 to 12; this pH range being recognized as most effective for achieving metallic ion reduction and in keeping the various reagents utilized in solution.

Thus, in one of its aspects, the present invention provides an aqueous solution useful in connection with a redox type spectrophotometric or colorimetric determination of uric acid in a biologic fluid. The solution contains either a multivalent metallic ion reducible to a lower valence state by uric acid or a water-soluble chelating compound capable of complexing with a metallic ion after reduction by uric acid to yield, in complexed form, a colored complex. If the solution being fashioned is the final reagent solution to which the biologic fluid is to be added, then it contains a combination of both the ion and the chelating compound. In any event, in keeping with this invention, the solution also contains, as an added constituent, imidazole or an alpha-amino acid. This constituent is present in an amount such that, when the solution contains a biologic fluid, an appropriate buffer system, and a multivalent metal ion, the protein in the fluid does not reduce the multivalent ions also present in the solution.

In accordance with a preferred aspect of the present invention, the solutions illustrated herein contain both the imidazole and alpha-amino acid. By including both of these ingredients, not only is protein interference effectively avoided but, additionally, the absorbance of the reagent blank (containing uricase) is lowered thereby increasing the sensitivity of the determination and the color stability of the test solution is also enhanced. The solutions of the present invention are considered to be particularly useful in connection with 2,2'-bicinchoninate method for uric acid determination. The combined use of imidazole and the amino acid has the further advantage that the solubility of the chelating compound is increased, particularly at the preferred pH range of 6.5–9.5.

The following example illustrates the present invention. All parts and percentages are by weight unless otherwise indicated.

Three solutions containing the following ingredients, each in 2 liters of deionized water, are prepared:

| A. Buffer | B. Dye | C. Copper |
|---|---|---|
| 0.4 gm $Na_2H_2$ ethylenediamine-tetraacetic acid.$2H_2O$ | 56.84 gm Imidazole | 1.67 gm Cupric sulfate pentahydrate |
| 18.0 gm Tris-hydroxymethylamino-methane | 6.68 gm Boric acid | |
| 12.2 gm Boric acid | 8.32 gm Alanine | |
| 100 ml Ethylene glycol | 100.0 gm Tris-(hydroxymethyl)-aminomethane | |
| 8.0 gm Polyvinylpyrrolidone | | |
| pH=8.5 | 30.0 gm Succinic acid | |
| | 3 ml Phenoxyethyanol | |
| | 18.68 gm Disodium 2,2'-bicinchoninate | |

A color reagent is first formulated by mixing together equal volumes of the dye solution B. and the copper solution C. within four hours prior to use. A uricase solution is also prepared by mixing 120 ml. of the buffer A. with 2 IU lyophilized uricase (Candida Utilis yeast) which is stored prior to use at 4° C. in a tightly capped vessel.

The test reagent is prepared by adding 0.1 ml. of serum sample to 1.0 ml. of buffer A. and incubating that solution at 37° C. for 15 minutes followed by 5 minutes of incubation at room temperature in a water bath. Then, 3 ml. of the color reagent is added thereto, the solution allowed to stand for 15 minutes at room temperature to permit color development and the absorbance then read at 562nm. The blank against which the test solution is read is prepared in an identical fashion except that 0.1 ml. of the serum sample is added to 1.0 ml of the uricase solution instead of to the buffer A.

Preferably, reagent blanks are prepared for both the test and blank solutions by using water as the sample in each of the above procedures instead of serum. Using such blanks for the purpose of setting absorbance at 0 will correct for any reductive interference which may be present in the uricase solution. Similarly, in order to construct a calibration graph, calibrator solutions are run in the test procedure in the same manner as serum.

With respect to this procedure, Beer's law is applicable up to a concentration of at least 20 mg/dl. For uric acid concentrations in excess of this value, isotonic saline (0.85 grams sodium chloride/dl) can be used to appropriately dilute the serum sample to bring the concentration within the desired range.

While the present invention has been illustrated with respect to a preferred embodiment, it is to be understood that it is not to be limited to only that embodiment. On the contrary, it is intended to cover all alternatives and modifications thereof as can be included within the spirit and scope of the invention as defined in the appended claims. For example, while the example has illustrated the invention in connection with the use of a copper--bicinchoninate redox system, the invention is considered applicable with respect to any redox system and, in particular, also to the phosphotungstic and neocuproine methods.

Furthermore, while the example has specifically shown the use of imidazole and alanine originally present in the solution containing the 2,2'-bicinchoninate, it is to be understood that these added constituents, or only one of them, can be originally included in either the buffer solution or the metallic ion solution or all three solutions can be preformulated and the imidazole and/or organic acid added thereto. In this respect, the important aspect is that the added constituent be present prior to the time at which the serum containing protein and uric acid is brought into contact with the multivalent ion.

Moreover, it is to be understood that the invention, though illustrated with respect to alanine as the amino acid, can be practiced with any other of the recognized water soluble alpha-amino acids. Furthermore, as to the amount of imidazole and/or amino acid employed, this must be sufficient to prevent the discussed protein interference and an appropriate concentration thereof can be determined by simple experimentation once the particular redox system has been selected. In general, based on the use of 0.1 ml. of serum, about 10 mg to 100 mg of added constituents is useful with about 50 mg being particularly preferred.

I claim:

1. In an aqueous solution useful in connection with a redox type spectrophotometric or colorimetric determination of uric acid in a biologic fluid comprising a multivalent metallic ion reducible to a lower valence state by uric acid and a water soluble chelating compound capable of complexing with said metallic ion after reduction by uric acid to yield, in complexed form, a colored complex; the improvement wherein said solution also contains, as an added constituent, imidazole, or a combination of imidazole and a water soluble alpha-amino acid, said constituent being present in an amount such that, when said solution contains a biologic fluid containing protein and uric acid, a buffer system such that the pH of the solution is 6 to 12, and a multivalent metal ion, said protein in said fluid does not significantly reduce said multivalent ions present in said solution.

2. The solution of claim 1 wherein the multivalent ion is divalent copper reducible by uric acid to monovalent copper and said chelating compound contains two aromatic rings, each of which has a heterocyclic nitrogen atom which combine in complexing with the monovalent copper ion.

3. The solution of claim 2 wherein the chelating compound is neocuproine or a 2,2'-bicinchoninate salt.

4. The solution of claim 3 wherein the chelating compound is disodium 2,2'-bicinchoninate.

5. The solution of claim 4 wherein said added constituent is imidazole.

6. The solution of claim 4 wherein said added constituent is a combination of imidazole and a water soluble alpha-amino acid.

7. The solution of claim 6 wherein said amino acid is alanine.

8. The solution of claim 7 wherein said buffer system maintains the pH of the solution at about 6.5-9.5 after the addition thereto of said sample of biologic fluid.

9. In an aqueous solution useful in connection with a redox type spectrophotometric or colorimetric determination of uric acid in a biologic fluid comprising a divalent copper ion reducible to a monovalent copper ion by uric acid, disodium 2,2'-bicinchoninate and a buffer system to maintain the pH of the solution at about 6.5-9.5 after the addition thereto of a sample of biologic fluid containing uric acid and protein; the improvement wherein said solution also contains imidazole and a water soluble alpha-amino acid in an amount such that said protein in said fluid does not significantly reduce said multivalent ions present in said solution.

10. The solution of claim 9 wherein said amino acid is alanine.

* * * * *